United States Patent [19]
Ishiguro et al.

[11] Patent Number: 5,501,217
[45] Date of Patent: Mar. 26, 1996

[54] CONTACT LENS FOR INTRAOCULAR OBSERVATION

[75] Inventors: Shinji Ishiguro, Aichi; Toshiharu Morino, Nagoya, both of Japan

[73] Assignee: Tomey Corporation, Nagoya, Japan

[21] Appl. No.: 244,382

[22] PCT Filed: Dec. 28, 1992

[86] PCT No.: PCT/JP92/01734

§ 371 Date: Jun. 9, 1994

§ 102(e) Date: Jun. 9, 1994

[87] PCT Pub. No.: WO94/14369

PCT Pub. Date: Jul. 7, 1994

[51] Int. Cl.$^6$ .......................................... A61B 3/16
[52] U.S. Cl. .................................... 128/645; 351/200
[58] Field of Search ........................... 128/645–652; 351/200, 205, 209, 212, 216

[56] References Cited

U.S. PATENT DOCUMENTS 3,487,679  1/1970  Yamamori ........................ 128/652
3,832,891  9/1974  Stuckey ............................ 128/652
4,766,904  8/1988  Kozin et al. ..................... 128/652

*Primary Examiner*—Angela D. Sykes
*Assistant Examiner*—John P. Lacyk
*Attorney, Agent, or Firm*—Armstrong, Westerman, Hattori, McLeland & Naughton

[57] ABSTRACT

A contact lens for intraocular observation including a lens body having a contact face to be brought into contact with cornea of an eyeball of a subject, and a lens support having a contact portion to be settled on sclera of the eyeball of the subject, the lens body and the lens support being assembled on each other by means of a slide mechanism so as to be movable relative to each other in the axial direction of lens, wherein the lens body is capable of pressing the cornea of the eyeball of the subject by movement thereof in the axial direction of lens relative to the lens support settled on the sclera of the eyeball of the subject. The contact lens of the present invention is of good operability and adapted to effectively prevent slipping of itself on the cornea of an eyeball.

8 Claims, 5 Drawing Sheets

CONTACT LENS FOR INTRAOCULAR OBSERVATION

TECHNICAL FIELD

The present invention relates to a contact lens for intraocular observation for use in diagnosis, treatment or the like with respect to an eyeball and, in particular, to a contact lens for intraocular observation which is advantageously used for observation, examination, operation or the like on an angle portion in an eyeball.

BACKGROUND ART

An angle portion is situated at peripheral edge of anterior chamber of an eyeball and of which abnormalities such as too wide or too narrow angle, open or closure angle and adhesion are related to intraocular pressure, occurrence of glaucoma or the like. In ophthalmology, therefore, examination on such angle portion is prevailing.

Since direct observation on an angle portion is difficult, it has hitherto been a usual practice to use a contact lens for gonioscopy as disclosed in Japanese Examined Patent Publication No. 13039/1974. However, when there is a closure or adhesion in the angle portion of a subject, even such a contact lens cannot allow observation on the inner part of the angle portion.

Therefore, usually, the angle portion of a subject is firstly observed using a contact lens for gonioscopy, and then, if closure or adhesion is found in the angle portion, an indentation gonioscopy 4 provided therein with a lens 2 as shown in FIGS. 7 and 8 is used to further observe the angle portion. A tip face 6 of the indentation gonioscopy 4 is brought into contact with the cornea of the subject and made to press it so as to enlarge the angle portion thereby allowing observation thereon.

With such a conventional technique, however, the observation work has been troublesome while at the same time inflicting much pain on a subject because the contact lens for gonioscopy should be changed with the indentation gonioscopy as required.

Further, an indentation gonioscopy of the conventional type is adapted to press a part of cornea periphery so as to enlarge a part of angle portion on the opposite side of the pressed part thereby allowing observation. Hence, it is likely that there is produced local strain or wrinkle in the cornea during the pressing operation, thus making observation unclear. Accordingly, the conventional gonioscope has involved a problem of difficulty in observation.

In addition, such an indentation gonioscopy is likely to slip on a subject eye upon pressing it; hence, it is very difficult to continuously press the target pressing position of cornea of an eyeball for observation. Accordingly, the conventional indentation gonioscopy has involved another problem of requiring a high technique and skill for observation.

The present invention has been made with the background of the foregoing circumstances. Thus, it is an object of the present invention to provide a contact lens for intraocular observation of very good operability, with which, besides observation on a subject eye in a normal state, observation can be made on the inner part of an angle portion as required if there is a closure or adhesion, while at the same time generation of strain or wrinkle in the cornea of a subject eye during observation can be advantageously avoided and a slip on the subject eye can be effectively prevented.

DISCLOSURE OF INVENTION

A contact lens for intraocular observation of the present invention is characterized by comprising a lens body having a contact face to be brought into contact with cornea of an eyeball of a subject, and a lens support having a contact portion to be settled on sclera of the eyeball of the subject, the lens body and the lens support being assembled on each other by means of a slide mechanism so as to be movable relative to each other in the axial direction of lens, wherein the lens body is capable of pressing the cornea of the eyeball of the subject by movement thereof in the axial direction of lens relative to the lens support settled on the sclera of the eyeball of the subject.

In such a contact lens for intraocular observation, preferably, the contact face of the lens body is of a substantially circular, spherical concave shape to be fitted with the cornea of an eyeball of a subject, while on the other hand the contact portion of the lens support is of a substantially annular shape to be positioned around the contact face of the lens body.

Yet, in the contact lens for intraocular observation according to the present invention, the slide mechanism is preferably provided with a stopper mechanism for restricting the amount of movement of the lens body relative to the lens support in the axial direction of lens. Alternatively, it is preferable that the lens body is removably assembled on the lens support, while at the same time a detachment-prevention mechanism is provided for preventing the lens body from detaching from the lens support.

Further, in the contact lens for intraocular observation according to the present invention, more preferably, the contact face of the lens body is made to have a circular, spherical concave shape having a diameter of not more than 11 mm which is smaller than the diameter of cornea of a subject.

BEST MODE FOR CARRYING OUT THE INVENTION

Hereinafter, the embodiments of the present invention will be described in detail with reference to the drawings in order to clarify the present invention more concretely.

Figure 1:
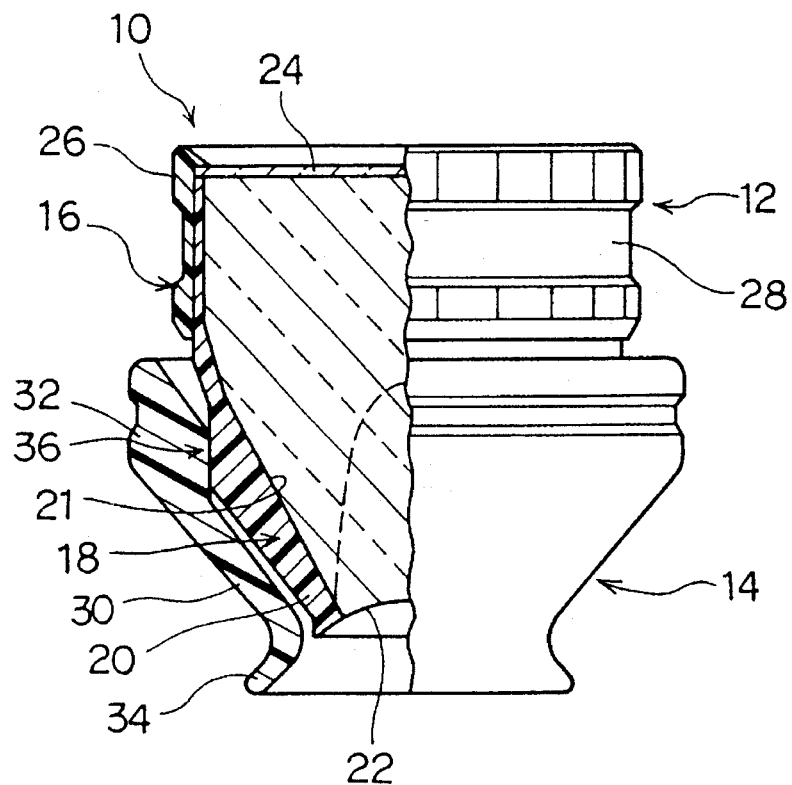
FIG. 1 is an elevational view half in section showing a contact lens for indentation gonioscopy as an embodiment of the present invention.
Figure 2:
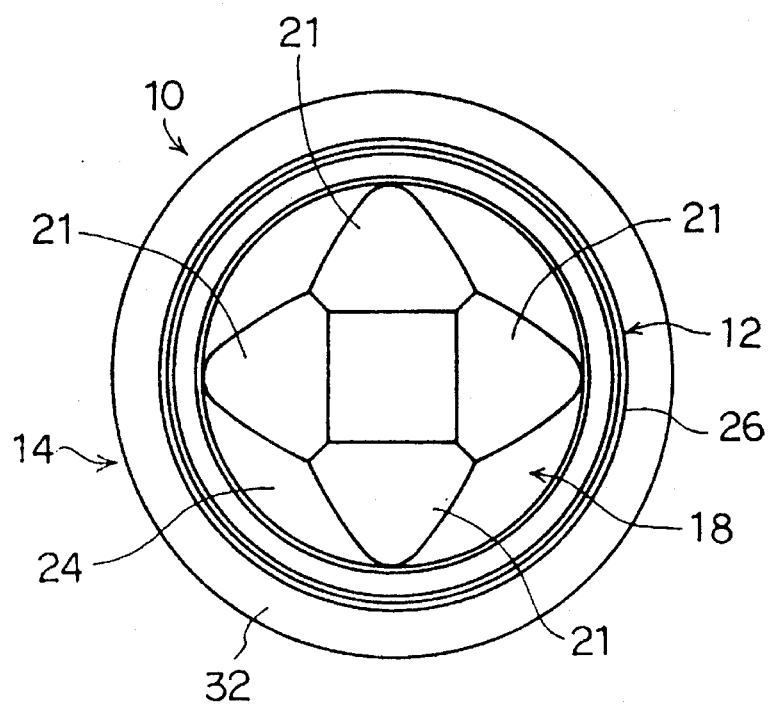
FIG. 2 is a plan view of the contact lens for indentation gonioscopy shown in FIG. 1.

FIGS. 1 and 2 show a contact lens for indentation gonioscopy 10 according to an embodiment of the present invention. The contact lens 10 is composed of a lens body 12 having an outward form of a substantially circular, short column of which outer perimeter is taperedly reduced at one axial end portion thereof, and a lens support 14 assuming, as a whole, a substantially cylindrical shape, the lens body 12 and the lens support 14 being assembled integrally.

In more detail, the lens body 12 includes a box 16 shaped substantially cylindrical as a whole, of which perimeter is taperedly reduced at one axial end portion thereof. Within this box 16 is fitted and accommodated a lens 18 formed from a transparent, light-transmissive material such as an acrylic material.

The inner periphery of a tapered cylinder portion 20 of the box 16 is circumferentially formed with four flat faces 21 at a relative angle of 90° in a circumferencial direction which are slanted at a predetermined angle with respect to a plane perpendicular to the axis of the box 16 and covered with aluminum coat by, for example, a vapor deposition technique to form four reflecting mirror faces 21. It should be noted that since the contact lens 10 of the present embodiment is for gonioscopy, each reflecting mirror face 21 is slanted desirably at about 62° with respect to a plane perpendicular to the axis of the box 16 to assure a good visibility of an angle portion.

Further, the outer perimeter of the lens 18 to be accommodated within the box 16 is taperedly reduced at one axial end of the lens 18 so as to be fitted with the inner peripheral shape of the box 16, and the tapered outer peripheral surface of the lens 18 is formed with four faces to be fitted with the reflecting mirror faces 21 of the box 16. Such a lens 18 is inserted and integrally fixedly fitted into the box 16 while being in close contact with the respective reflecting mirror faces 21 formed on the box 16.

Yet, the axial end face on the tapered side of the lens body 12 formed by thus integrating the lens 18 with the box 16 assumes a circular, spherical concave shape thereby defining a contact face 22. It should be noted that, in the present embodiment in particular, such a contact face 22 is made to have a diameter of not more than 11 mm which is smaller than that of the cornea of an ordinary adult person (usually 11.5 to 12 mm), whereby the contact face 22 is adapted to advantageously press the cornea of an eyeball when brought into contact with it, as described later.

On the other axial end face of the lens 18 and box 16 is superposed a transparent protective film 24 so as to cover the end faces of the lens 18 and box 16. The protective film 24 is integrally mounted thereon by being fixed at its peripheral portion with a cylindrical fixing ring 26 which is fixedly fitted on the outer periphery of the box 16. Moreover, such a fixing ring 26 is formed at its outer peripheral face in the axial central part thereof with a recessed groove 28 extending circumferentially so as to facilitate holding with fingers.

On the other hand, the lens support 14 has a tapered cylinder portion 30 at its axial intermediate portion which assumes a tapered cylindrical shape. The tapered cylinder portion 30 is provided integrally with a thick cylinder portion 32 at its larger diameter opening end portion while at its smaller diameter opening end portion a contact portion 34 extending outwardly like a skirt.

As seen in the drawings, the lens body 12 is inserted into and assembled on the lens support 14 from the side of the cylinder portion 32 thereby constituting the objective contact lens for indentation gonioscopy 10.

Here, the cylinder portion 32 of the lens support 14 is made to have an inner diameter substantially the same as the outer diameter of the axial intermediate portion of the box 16 constituting the lens body 12. For this reason, when the lens body 12 is to be assembled on the lens support 14, the lens body 12 is adapted to be displaceable relative to the lens support 14 in the axial direction of lens with guidance by the inner peripheral face of such a cylinder portion 32. As is apparent from this description, in the present embodiment a slide mechanism is constituted by a slide portion 36 defined between the outer peripheral face of the axial intermediate portion of the lens body 12 and the inner peripheral face of the cylinder portion 32 of the lens support 14.

Further, the tapered cylinder portion 30 of the lens support 14 is formed at a taper angle substantially the same as that of the outer peripheral face of the tapered cylinder portion 20 of the box 16 constituting the lens body 12. For this reason, the outer peripheral face of the tapered cylinder portion 20 of the box 16 of the lens body 12 is made to abut on the inner peripheral face of the tapered cylinder portion 30 of the lens support 14, whereby displacement of the lens body 12 relative to the lens support 14 in the axial direction of lens can be restricted. As is apparent from this description, in the present embodiment a stopper mechanism is formed between the inner peripheral face of the tapered cylinder portion 30 of the lens support 14 and the outer peripheral face of the tapered cylinder portion 20 of the box 16 of the lens body 12.

Yet, the contact portion 34 of the lens support 14 is opened with a diameter larger than that of the cornea of an eyeball and extended like a skirt to have a shape to be substantially fitted with the outer peripheral face of sclera of an eyeball. For this reason, when the contact portion 34 is brought into contact with the sclera of a subject eyeball, the contact portion 34 is adapted to be advantageously settled on the sclera.

To be described next is a method of gonioscopy using the contact lens 10 of the structure described above.

Figure 3:
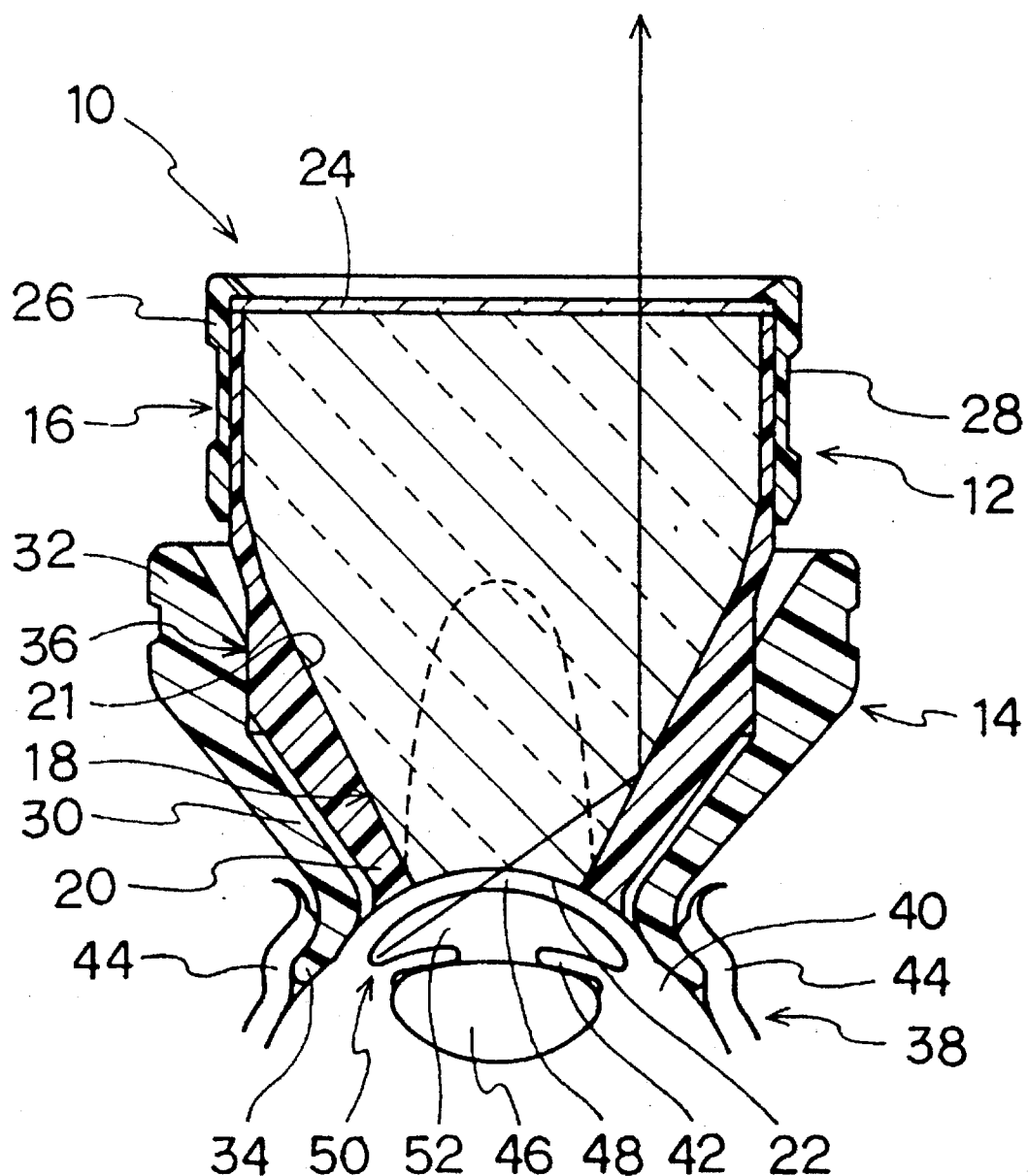
FIG. 3 is an explanatory view for illustrating a method of gonioscopy with use of the contact lens for indentation gonioscopy shown in FIG. 1.

In gonioscopy using the contact lens 10, firstly, the contact portion 34 of the lens support 14 is brought into contact with and settled on the surface of sclera 40 of an subject eyeball 38, as shown in FIG. 3, thereby fixedly holding the lens support 14 relative to the subject eyeball 38. In FIG. 3, numeral 42 denotes iris, 44, 44 upper and lower eyelids, and 46 crystalline lens.

Thereafter, the contact face 22 of the lens body 12 is brought into contact with the cornea of the subject eyeball 38 by making the lens body 12 slide relative to the lens support 14 toward the subject eyeball 38.

Thus, by bringing the contact face 22 of the lens support 12 into contact with the surface of the cornea 48 of the subject eyeball 38, light is reflected at the reflecting mirror faces 21 of the lens body 12 and runs through the lens body 12 as indicated by the arrow in FIG. 3, whereby an angle portion 50 of the subject eyeball 38 can be observed.

Figure 4:
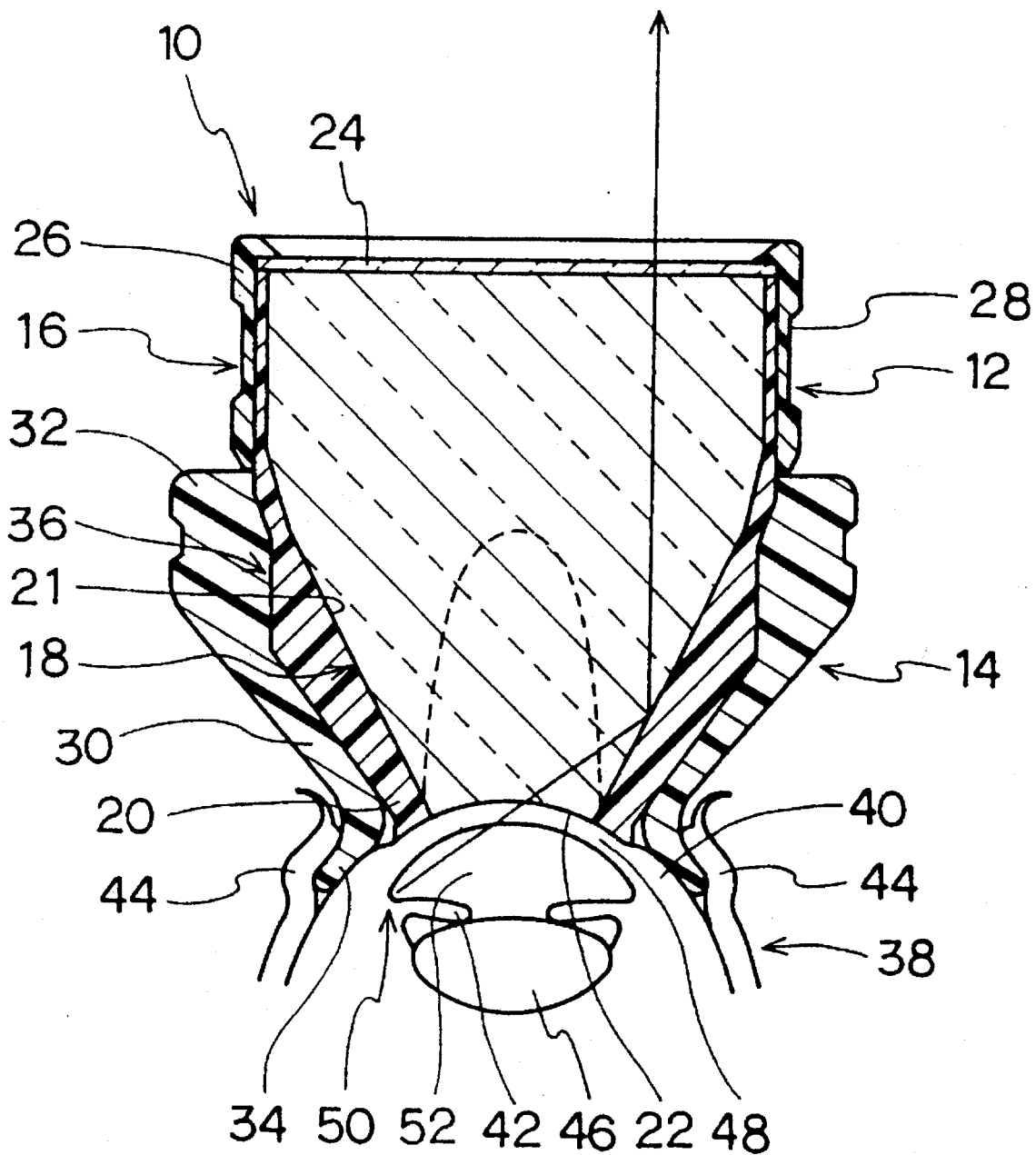
FIG. 4 is an explanatory view for illustrating a method of gonioscopy with use of the contact lens for indentation gonioscopy shown in FIG. 1, the method being different from that shown in FIG. 3.

If the angle portion 50 is found to have a closure or adhesion by such observation, the inner part of the angle portion 50 remains unobserved by this observation. Then, in such a case the lens body 12 is made to further slide relative to the lens support 14 toward the subject eyeball 38, as shown in FIG. 4.

As a result, such an operation causes the contact face 22 of the lens body 12 to press against the surface of the cornea 48 of the subject eyeball 38 so as to bring pressure thereon, whereby the iris 48 is pressed toward the eyegrounds and, hence, the angle portion 50 is enlarged. Therefore, the thus enlarged angle portion 50 is observed with light reflected at the reflecting mirror faces 21 of the lens body 12 and running through the lens body 12 thereby permitting easy observation even on the inner part of the angle portion 50.

Since, in the contact lens 10 of the present embodiment in particular, the contact face 22 of the lens body 12 is made to have a diameter smaller than that of the cornea 48 by a predetermined amount as described above, making such a contact face 22 press against the central portion of the cornea 48 can effectively bring pressure thereon, whereby the angle portion 50 can be advantageously enlarged.

Further, in this contact lens 10 the lens body 12 is supported relative to the subject eyeball 38 by the lens support 14 settled on the sclera 40 and, hence, the lens body 12 can be prevented from slipping on the subject eyeball 38 very effectively, thus rendering such an observation operation easy.

Figure 7:
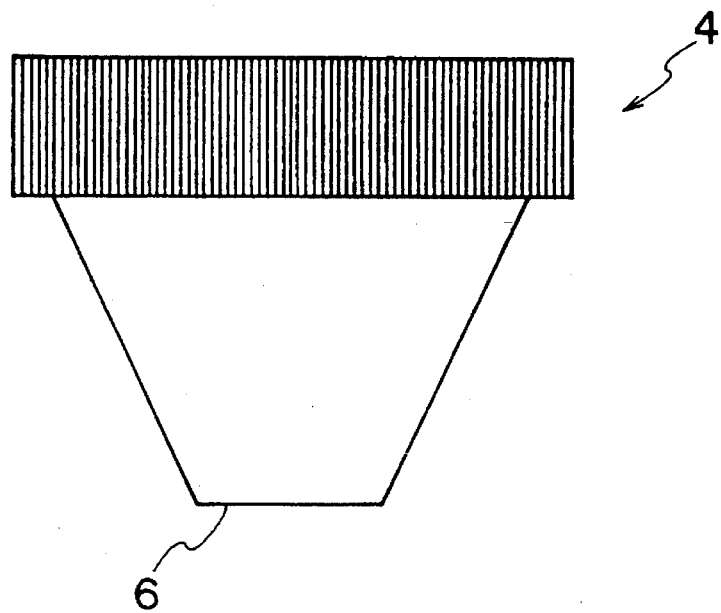
FIG. 7 is a side elevational view showing a conventional contact lens for indentation gonioscopy for use in observation on the angle portion of an eyeball.
Figure 8:
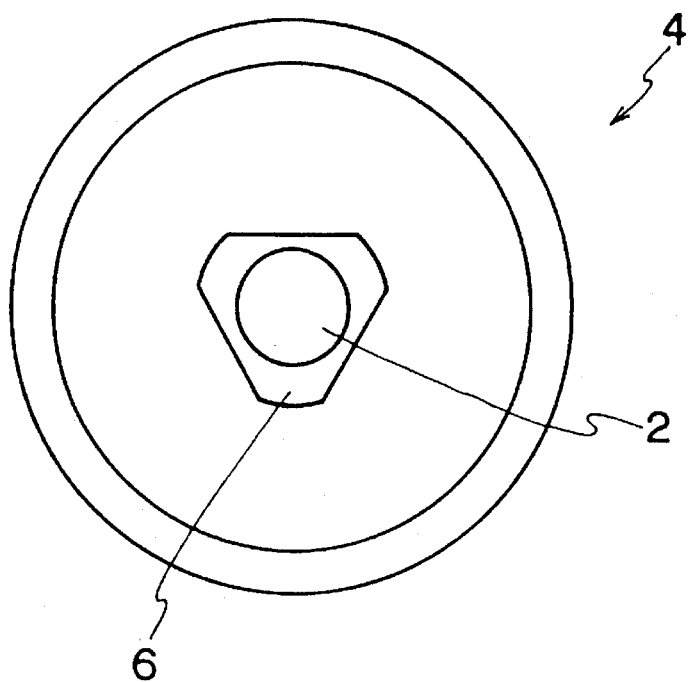
FIG. 8 is a plan view of the contact lens for indentation gonioscopy shown in FIG. 7.

Yet, the contact lens 10 can extensively press the central portion of the cornea 48 of the subject eyeball 38 so as to enlarge the angle portion 50. Hence, generation of wrinkles or the like on the cornea 48 can be advantageously mitigated or inhibited as compared with a conventional indentation gonioscopy (refer to FIGS. 7 and 8), which requires to locally bring pressure on the cornea. Besides, an observable extent can be expanded thereby assuring easy observation.

The contact lens 10 of the present embodiment in particular has the four reflecting mirror faces 21 circumferentially formed at a relative angle of 90° and, hence, the overall periphery of the angle portion 50 can be observed simultaneously.

In addition, in the present embodiment in particular, the stopper mechanism is provided between the lens body 12 and the lens support 14 for restricting the amount of movement of the lens body 12 relative to the lens support 14. Hence, when pressure is brought on the cornea 48, there is no likelihood of bringing too much pressure thereon, thereby assuring excellent safety.

Figure 5:
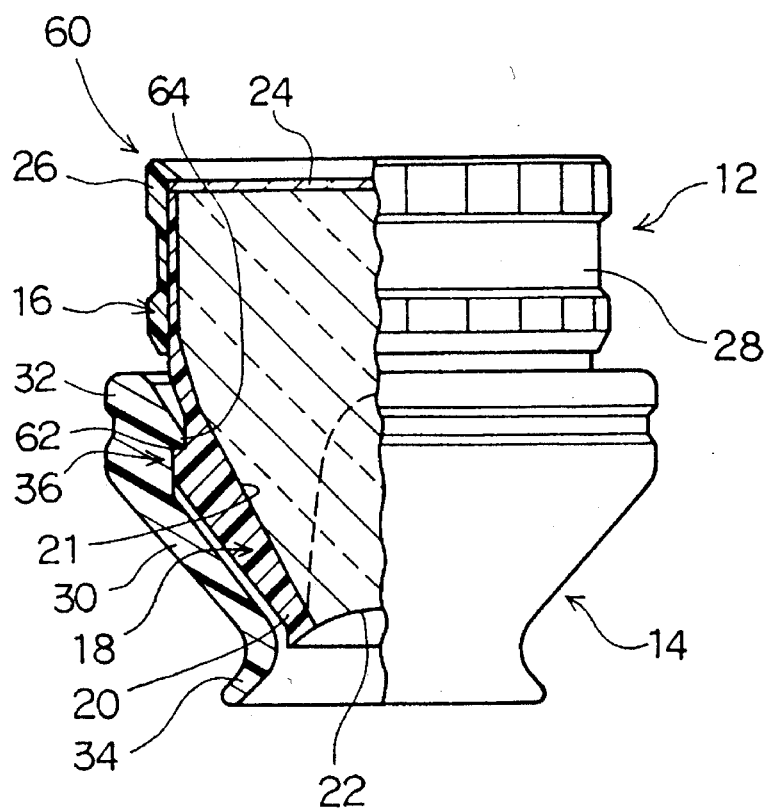
FIG. 5 is an elevational view half in section showing a contact lens for indentation gonioscopy as an another embodiment of the present invention.
Figure 6:
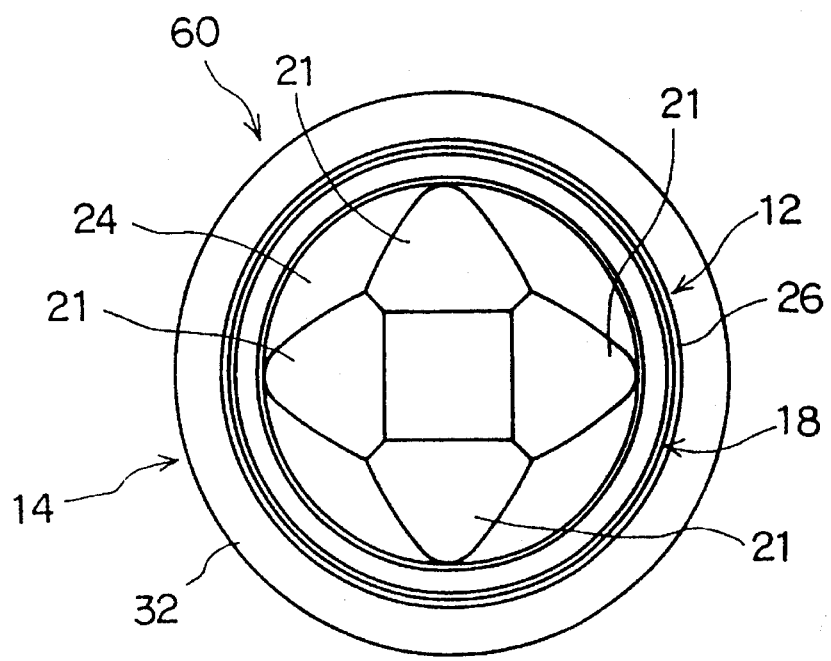
FIG. 6 is a plan view of the contact lens for indentation gonioscopy shown in FIG. 5.

Next, a contact lens for indentation gonioscopy 60 is shown in FIGS. 5 and 6 as an alternative embodiment of the present invention. It should be understood that this embodiment is a specific example wherein the contact lens 10 of the above-mentioned first embodiment is further added with a detachment-prevention mechanism, and that members and portions thereof of structures similar to those of the first embodiment are denoted by the same numerals in these figures so as to omit detailed descriptions thereon.

In detail, in the present embodiment is provided an engagement groove 62 shaped into a continuously extending recessed groove in a substantially axial central portion of a box 16 constituting a lens body 12. On the other hand, there is provided an engagement projection 64 of the shape projecting radially inwardly which is circumferentially continuously extending in an open end portion of a cylinder portion 32 of a lens support 14.

In the assembled condition wherein the lens body 12 is inserted into the lens support 14, the lens body 12 is allowed to move relative to the lens support 14 by a predetermined amount in the axial direction of lens, while in contrast when the lens body 12 is moved relative to the lens support 14 in the detaching direction (i.e, the direction which does not allow exertion of the stopping function produced by the contact of the outer peripheral face of a tapered cylinder portion 20 of the box 16 with the inner peripheral face of a tapered cylinder portion 30 of the lens support 14), the engaging action of the engagement projection 64 with respect to the engagement groove 62 prevents the lens body 12 from detaching from the lens support 14.

Therefore, the contact lens 60 having such a detachment-prevention mechanism according to the present embodiment effectively provides, as well as all the effects offered by the first embodiment, the following effects. The manipulability in observation, storage, transit or the like can be advantageously improved; the operability in observation can also be advantageously improved; and there can effectively be avoided damages attributable to unexpected detachment of the lens body 12 from the lens support 14, or the like.

It is worth noting that in the case where such an engagement mechanism is provided, forming the lens support 14 from a deformable material such as synthetic resin would permit easy assemblage of the lens body 12 on the lens support 14.

Further, if at least a portion of the lens support 14 which constitutes the engagement mechanism together with the lens body 12 is formed from a member which allows elastic deformation, it is possible to make the lens support 14 and lens body 12 readily detachable from each other.

If the lens support 14 and lens body 12 are made readily detachable from each other, it would be possible to separate them from each other at an appropriate occasion and to wash them separately, which is desirable from the view point of sanitation.

While the embodiments of the present invention have been described in detail, these are for illustration only and, hence, the present invention must not be interpreted to be limited only to these embodiments.

For instance, the slide mechanism for guiding the lens body relative to the lens support in the axial direction of lens is not limited to the slidable structure of cylindrical faces as in the above embodiments.

Further, the stopper mechanism for restricting the amount of movement of the lens body relative to the lens support is not limited to the abutting structure of tapered faces as in the above embodiments.

Yet, the detachment-prevention mechanism for preventing the lens body from detaching from the lens support is not limited to the engagement mechanism comprising the recessed portion and projecting portion which are extending circumferentially continuously, as in the above embodiments.

Yet still, the structure of reflecting mirror faces 21 is not limited to that of the embodiments, and the number, shape or slanting angle thereof and the like can be appropriately altered.

Further, the contact portion of the lens support is not limited to have the annular shape as in the above embodiments, and it is possible to form the contact portion of the shape having, for example, a pair of arcs which can be brought into contact only with upper and lower portions of sclera which are situated as vertically sandwiching the cornea.

The stopper mechanism for restricting the amount of movement of the lens body relative to the lens support and the detachment-prevention mechanism for preventing the lens body from detaching from the lens support, as exemplified in the above embodiments, are each provided as required.

In addition, the present invention can, of course, be advantageously applied to a contact lens for observation on portions of an eyeball other than an angle portion, or to a contact lens for use in operation or treatment with a laser surgical unit with respect to an angle portion or the like.

The present invention can, although not enumerated, be realized in modes imparted with various modifications, alterations, improvements or the like based on the knowledge of those skilled in the art. It is needless to say that any of such modes is included in the scope of the present invention unless it departs from the spirit of the present invention.

As is apparent from the foregoing descriptions, with the contact lens for intraocular observation according to the present invention, the lens body, which is supported by the lens support settled on the sclera of an eyeball, is brought into contact with the cornea thereof at its contact face; hence, observation can be effected on the angle portion of an eyeball in a normal state, while even the inner part of the angle portion can be observed by enlarging the angle portion by moving the lens body to slide relative to the lens support so as to press the contact face thereof against the cornea of the eyeball. Thus, it is possible to appropriately effect observation not only on an eyeball in a normal state but also on the inner part of an angle portion of the eyeball with the cornea thereof under pressure, thus enabling very easy and smooth observation.

Further, with such a contact lens for intraocular observation, the lens body is supported on the sclera of an eyeball which is relatively hard through the lens support and capable of extensively bringing pressure on the central portion of the cornea. Hence, even when pressed against the cornea, the lens body can be effectively prevented from slipping on the cornea while advantageously mitigating or avoiding generation of wrinkles or the like on the cornea, whereby improvements in operability can be attained more advantageously.

With the contact lens for intraocular observation according to claim 2 wherein the contact portion of the lens support is shaped annular and positioned around the contact face of the lens body, there can be effectively obtained a large support strength of the lens support for supporting the lens body on an eyeball.

Yet, with the contact lens for intraocular observation according to claim 3 wherein the stopper mechanism is provided for restricting the amount of movement of the lens body relative to the lens support, the cornea of an eyeball can be prevented from being excessively pressed there by assuring safety advantageously.

Yet still, with the contact lens for intraocular observation according to claim 4 wherein the detachment-protection mechanism is provided for avoiding detachment of lens body from the lens support, both the manipulability of the contact lens and the operability thereof during observation can be improved advantageously.

Furthermore, the contact lens for intraocular observation according to claim 5 wherein the contact face of the lens body is formed into a circular, spherical concave shape having a diameter less than 11 mm, effective pressure can be brought on the central portion of cornea of an eyeball to advantageously enlarge the angle portion thereof, thus assuring easier observation on the angle portion.

Industrial Applicability

The contact lens for intraocular observation according to the present invention can be effectively prevented from slipping on the cornea of an eyeball with superior operability and is, hence, useful for a contact lens for intraocular observation which is employed in diagnosis, treatment or the like with respect to an eyeball.

We claim:

1. A contact lens for intraocular observation comprising a lens body having a contact face for contact with a cornea of an eyeball of a patient, and a lens support having a contact portion to be settled on a sclera of the eyeball of the patient, the lens body and the lens support being assembled on a slide mechanism means so as to be movable relative to each other in an axial direction of the lens, wherein the lens body is adapted to be pressed on the cornea of the eyeball of the patient by movement of the lens in an axial direction of the lens relative to the lens support settled on the sclera of the eyeball of the patient.

2. The contact lens for intraocular observation as set forth in claim 1, wherein said contact face of said lens body is of a substantially circular, spherical concave shape for fitting with the cornea of the eyeball of the patient, while said contact portion of said lens support is of a substantially annular shape for positioning around the contact face of the lens body.

3. The contact lens for intraocular observation as set forth in any one of claims 1 to 2, wherein said slide mechanism means is provided with a stopper mechanism for restricting the amount of movement of said lens body relative to said lens support in the axial direction of the lens.

4. The contact lens as set forth in any one of claims 1 or 2, wherein said lens body is removably assembled on said lens support, with a detachment-prevention mechanism for preventing the lens body from detaching from the lens support.

5. The contact lens for intraocular observation as set forth in any one of claims 1 or 2, wherein said contact face of sad lens body is of a circular, spherical concave shape having a diameter of not more than 11 mm.

6. The contact lens as set forth in claim 3, wherein said lens body is removably assembled on said lens support, with a detachment-prevention mechanism for preventing the lens body from detaching from the lens support, 7. The contact lens for intraocular observation, as set forth in claim 3, wherein said contact face of said lens body is of a circular, spherical concave shape having a diameter of not more than 11 mm.

8. The contact lens for intraocular observation, as set forth in claim 4, wherein said contact face of said lens body is of a circular, spherical concave shape having a diameter of not more than 11 mm.

* * * * *